(12) United States Patent
Skinner et al.

(10) Patent No.: US 6,456,888 B1
(45) Date of Patent: Sep. 24, 2002

(54) GEOMETRY FOR COUPLING AND ELECTRODE TO A CONDUCTOR

(75) Inventors: Dwight Skinner, St. Anthony; Michael P. Brenzel, St. Paul, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 183 days.

(21) Appl. No.: 09/642,171

(22) Filed: Aug. 18, 2000

(51) Int. Cl.⁷ .................................................. A61N 1/05
(52) U.S. Cl. ........................................ 607/116; 607/122
(58) Field of Search ................................ 607/116, 119, 607/122; 140/14, 112

(56) References Cited

U.S. PATENT DOCUMENTS

| | | | |
|---|---|---|---|
| 4,161,952 A | 7/1979 | Kinnery et al. | 128/786 |
| 4,328,812 A | 5/1982 | Ufford et al. | 128/786 |
| 4,381,014 A | 4/1983 | Sandstrom et al. | 128/786 |
| 4,432,377 A | 2/1984 | Dickhudt | 128/786 |
| 4,559,951 A | 12/1985 | Dahl et al. | 128/642 |
| 4,590,950 A | 5/1986 | Iwaszkiewicz et al. | 128/786 |
| 4,592,372 A | 6/1986 | Beranek | 128/786 |
| 4,934,049 A | 6/1990 | Kiekhafer et al. | 29/883 |
| 4,944,088 A | 7/1990 | Doan et al. | 29/858 |
| 4,947,866 A | 8/1990 | Lessar et al. | 128/784 |
| 5,014,720 A | 5/1991 | Barcel et al. | 128/786 |
| 5,115,818 A | 5/1992 | Holleman et al. | 128/784 |
| 5,330,522 A | 7/1994 | Kreyenhagen | 607/122 |
| 5,522,872 A | 6/1996 | Hoff | 607/119 |
| 5,609,622 A | 3/1997 | Soukup et al. | 607/122 |
| 5,676,694 A * | 10/1997 | Boser et al. | 607/122 |
| 5,755,762 A | 5/1998 | Bush | 607/122 |
| 5,796,044 A * | 8/1998 | Cobian et al. | 607/119 |
| 6,018,684 A | 1/2000 | Bartig et al. | 607/122 |
| 6,295,476 B1 * | 9/2001 | Schaenzer | 607/122 |

* cited by examiner

*Primary Examiner*—Carl Layno
(74) *Attorney, Agent, or Firm*—Thomas J. Nikolai; Nikolai & Mersereau, P.A.

(57) ABSTRACT

A method for securing a coil or cable conductor to an electric element including an implantable electric element having a longitudinal edge electrically coupled to a coil or cable conductor. The coil or cable having filars with ends configured to contact the longitudinal edge of the electric element. The ends secured to the longitudinal edge by welding, soldering or an electrically conductive adhesive.

38 Claims, 4 Drawing Sheets

GEOMETRY FOR COUPLING AND ELECTRODE TO A CONDUCTOR

FIELD OF THE INVENTION

The present invention relates generally to lead assemblies for medical devices, and more specifically to a method and apparatus for providing a secure electrical connection between wound elements, as found in unifilar and multifilar coil conductors, and electric elements, such as lead connector pins, electrodes, sensors and various other elements employed in lead assemblies for implantable medical devices.

BACKGROUND OF THE INVENTION

Implantable leads form an electrical connection between a pulse generator or other electronic device and a tissue or structure in the body. For example, leads transmit electric signals used to stimulate cardiac or nerve tissue in one direction and signals generated by sensors placed in proximity to particular organs or tissues in the opposite direction. Leads typically include one or more electric elements at the lead's distal end. The electric elements are designed to form an electrical connection with a tissue or organ. Most leads also include a lead connector pin at the lead's proximal end. Lead connector pins are adapted to electrically and mechanically connect leads to the pulse generators or other electronic medical devices. A flexible conductor connects the electric element to the lead connector pin. Commonly, the flexible conductor takes the form of a single or multifilar wire coil. Although, there is an increasing interest in using stranded cables as conductors. Regardless of the form, the flexible conductors are typically surrounded by an insulating layer of material. Together, the flexible conductor and the insulating layer form the lead body. The lead body couples the lead connector pin at the proximal end with the electric element at the distal end.

Manufacturing leads is costly. Forming a secure electrical junction between the conductors and electric elements has proven difficult and time consuming. Laser welds are commonly used to connect the filars or wires that make up the conductors to electric elements. The conductor's filars are typically helically wound into a coil for increased reliability. Laser welding the coiled filars to electric elements typically requires that the end of a coil be ground flat. Grinding the ends flat allows sufficient contact between the coil and the electrical element to weld the two together with a butt joint. Grinding increases the time, complexity and cost of manufacture. Further, welding requires the synchronized rotation of the conductor and electric element to weld at the various points around their circumference. The rotating also adds to the time, complexity and costs of manufacture. Alternatively, ring electrodes are connected to a conductor by etching away a region of insulator, applying a coating of electrically conductive adhesive, and then placing the ring electrode around the conductor. This method is also time consuming and expensive. Hence, there exists a need to improve the manufacturing techniques used to secure electric elements to conductors in leads to reduce the time, complexity and cost.

In addition, current manufacturing techniques do not allow welding an electrical element to a coil without adding elements that increase the lead's diameter near the weld. In application, a uniform diameter weld would result in a smaller lead. A smaller diameter lead is desired to allow placement in restricted spaces such as cardiac veins or the epidural space to reduce the effects of implanted lead on the patient. Further, a smaller lead allows for a smaller introducer that reduces the trauma associated with implantation and similarly a smaller removal sheath when explanting the lead. Hence, there exists a need to reduce the diameter of the welds used to secure electric elements to conductors in implantable medical leads.

The present invention meets these needs and provides other advantages and improvements that will be evident to those skilled in the art.

SUMMARY OF THE INVENTION

The present invention provides a uniform diameter junction for an implantable lead and reduces the time, complexity and costs of producing implantable electrical leads by allowing the use of a straight line weld of the conductors to the electric elements. In addition, the junction typically results in a uniform diameter connection between the lead body and the electric element.

In accordance with the present invention, a method and lead design are provided for longitudinally securing the cut ends of a conductor to an electric element. The present invention's method for manufacturing an implantable medical device leads includes a conductor having at least one filar and an electric element having a longitudinal edge. The electric element can be a ring electrode, a terminal pin, a splice ring, a terminal ring, a lead connector pin, a sensor or other implantable medical device commonly attached to leads. The filars can be spirally wound into the conductor at a substantially constant pitch. The filars are cut in a direction parallel to a longitudinal axis of the conductor to form at least one collinear cut end. The collinear cut end is parallel to the longitudinal axis of the conductor. The ends are secured to the longitudinal edge of the electric element to provide an electrical connection. The cut ends can be secured to the electrical element by laser welding, resistance welding, soldering, swaging, electrically conductive adhesives, micro arc welding or by other methods known to those skilled in the art. In addition, the longitudinal edge can combine with a second edge to define a notch. The second edge is configured to have a pitch corresponding to the pitch of the filars. The corresponding pitch allows one of the plurality of filars to abut the second edge over the distance that the electric element and the conductor are coextensive. Further, the plurality of filars can embedded in an elongated, flexible elastomeric insulator. The insulator can define a lumen adapted to receive a stylet for guiding the lead into the patient. A portion of the insulator may be removed from the conductor's proximate end prior to welding. Typically, the insulator is removed mechanically or by chemical etching.

The present invention further discloses an implantable lead for a medical device. The implantable lead includes at least one conductor and one or more electric elements. The conductor has one or more filars wherein each filars terminate in an end. The ends are typically generated by cutting using any of a number of techniques known to those skilled in the art. The ends are cut so as to be collinearly oriented in a direction parallel to a long axis of the conductor. The filars can be spirally wound into the conductor at a substantially constant pitch. The electrical element also has a longitudinal edge. The longitudinal edge is configured to contact the cut ends and the cut ends are secured to the longitudinal edge, typically in a laser-welding step. When the filars are wound at a substantially constant pitch, the electrical element can have a second edge having a pitch corresponding to the pitch of the filars. The longitudinal edge and a second edge of the electric element cooperate to define a notch extending inwardly from one end of the electric element. The notch is shaped so that one of the plurality of filars abuts the second edge over the distance that the electric element and the conductor are coextensive.

DETAILED DESCRIPTION OF THE INVENTION

The present invention is applicable to a variety of implantable medical devices utilizing an electric current to stimulate selected body tissues or to transmit signals from a sensor or electrode contacting selected tissue to the medical device. The invention is described in the context of an electrode on a cardiac pacing lead as a specific example for illustrative purposes only. The appended claims are not intended to be limited to any specific end use, example or embodiment described in this specification. It will be understood by those skilled in the art that the invention may be used to provide electrically and mechanically secure connections between wound conductors and electrical elements in a wide variety of implantable leads including, but not limited to, pacing leads, sensing leads, defibrillation leads, unipolar leads, multipolar leads, and leads with extendable positive helix fixation electrodes.

Figure 1:
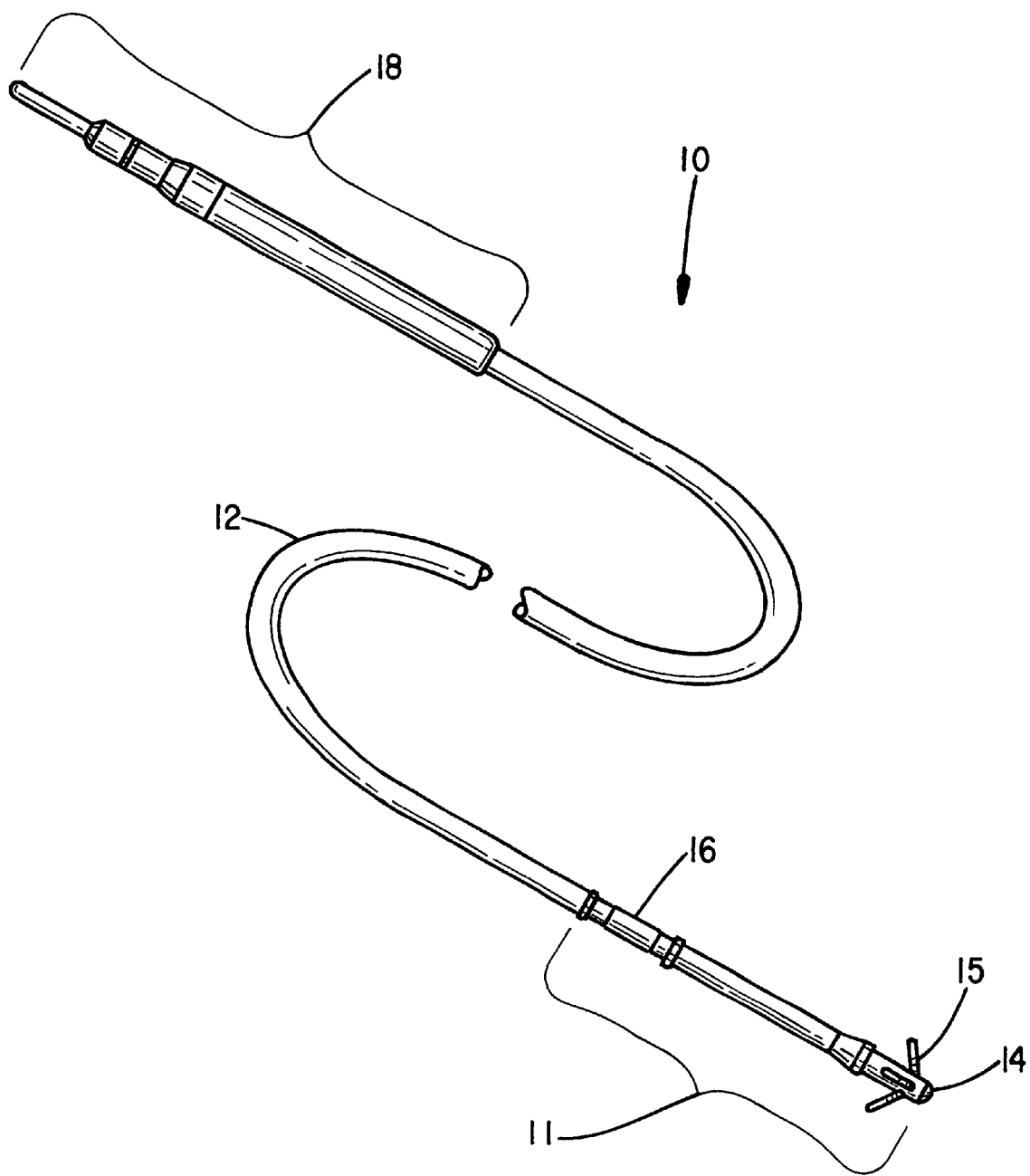
FIG. 1 is a perspective view of an implantable lead in which an embodiment of the present invention is practiced.

FIG. 1 illustrates a unipolar lead 10 made in accordance with the present invention. Lead 10 consists of an electrode assembly 11, a lead body 12, and a lead connector pin 18. Lead 10 is designed to facilitate insertion through a selected vein and then guiding electrode assembly 11 into the right ventricle of the heart or alternatively into a branch of the great coronary vein. Electrode assembly 11 then provides a pacing electrical stimulus to the heart. For exemplary purposes, electrode assembly 11 includes a tip electrode 14, a ring electrode 16 and tines 15. Electrode assembly 11, as shown, is configured to be secured within the trabeculae of the right ventricle by tines 15. Tip electrode 14 is typically a cathode. Ring electrode 16 can be an anode or a sensor for measuring biological parameters. Lead body 12 is typically elongated and flexible enabling the lead to be directed through the veins and heart of the patient. In its most basic form, lead body 12 includes one or more conductors (described in more detail below) covered by an insulator. The conductors transmit an electrical current to and/or from a tissue. The insulator prevents electrical leakage or short circuits. The insulator can be any of a variety of materials, including silicone, polyurethanes, fluoropolymers or other polymeric materials known to those skilled in the art. The insulators are generally selected based on biocompatibility, biostability and durability. Lead connector pin 18 is configured to be received by a pulse generator (not shown). The pulse generator may itself be implantable. Typically, the lead connector pin conforms to IS-1 when used to connect the lead to a pacemaker. The pulse generator can be a neurological stimulator, a cardiac pacemaker, a defibrillator, or other device transmitting an electrical stimulus to a tissue or organ.

Figure 2A:
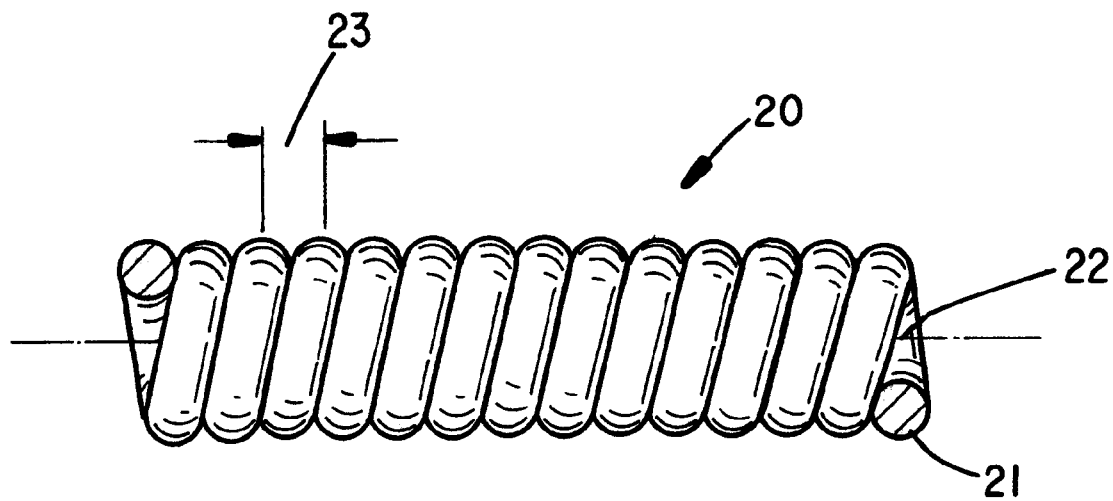
FIG. 2A illustrates a fragmentary view of a unifilar conductor used in a unipolar lead of FIG. 1.
Figure 2B:
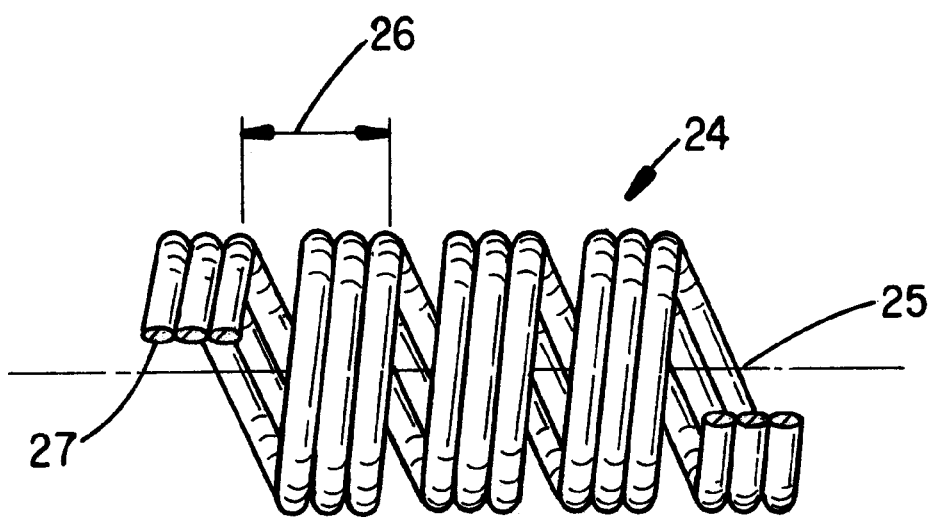
FIG. 2B illustrates a fragmentary view of a multifilar conductor used in a unipolar lead as in FIG. 1.

FIGS. 2A and 2B illustrate details of unifilar and multifilar wound conductors. A unifilar conductor 20 and a multifilar conductor 24 are both shown in unipolar embodiments. The conductors typically extend the length of lead body 12. Conductors electrically and, to a lesser degree, mechanically connect lead connector pin 18 to the electrodes 14 and sensor 16. The conductors are typically composed of single or multiple small wires or filars. The filars are typically made of stainless steel, MP35N, drawn-brazed-strand (DBS) or other electrically conductive materials known those skilled in the art. The filars typically range in size from 0.001 inch to 0.015 inch in thickness and typically are round, square or rectangular in cross-sectional shape. Unifilar conductor 20, shown in FIG. 2A, has a single wire or filar 21 wound around a central axis 22 to define a lumen. The helical winding of filar 21 around axis 22 creates a wound diameter and a pitch. The wound diameter defined as the diameter of the entire coil in cross section. Coiled conductors used in pacing leads typically have wound diameters between 0.010 inch and 0.125 inch, depending on the specific application. The pitch defined as a distance 23 a filar travels along the conductor's longitudinal axis in making one full wind around the axis. The pitch can vary with the physical dimensions and characteristics of the filar and/or the requirements for a particular application. Multifilar conductor 24, as shown in FIG. 2B, has more than one filar. Specifically, multifilar conductor 24 is a trifilar conducting coil constructed of three wires or filars 28 spiral wound in parallel around a central axis 25. The winding of filars 27 around axis 25 also creates a pitch. The pitch defined as a distance 26 a particular filar travels along the conductor's longitudinal axis in making one full wind around the axis. The pitch can vary with the number of filars 27, the physical characteristics of the filars and/or the requirements of the application.

Figure 3:
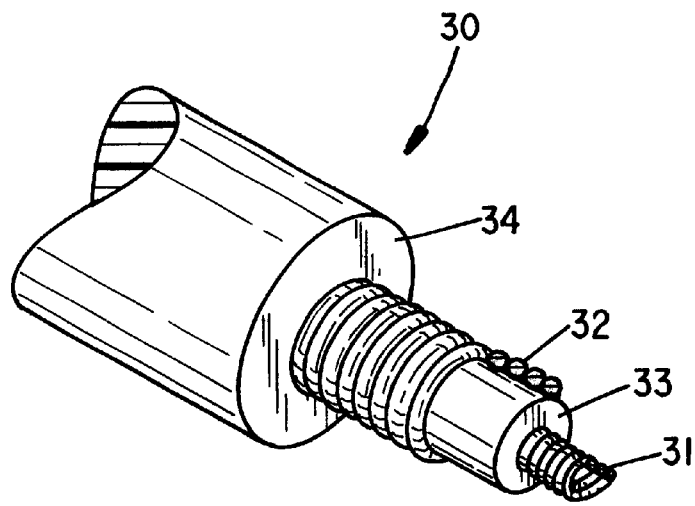
FIG. 3 illustrates a fragmentary view of a multifilar conductor used in a bipolar lead as in FIG. 1.

FIG. 3 illustrates a fragment of a bipolar lead 30. A bipolar lead has two conductors. Bipolar lead 30 has an inner conductor coil 31 coaxially disposed within the outer conductor coil 32. When using the lead body design of FIG. 3, outer conductor coil 32 is typically connected to a proximal sensing electrode and inner conductor coil 31 is connected to a distal tip electrode 14 (FIG. 1). The inner and outer coils of bipolar lead 30 can be either unifilar or multifilar. Inner conductor coil 31 has a smaller wound diameter than outer conductor coil 32. An insulator 33 is disposed between inner conductor coil 31 and outer conductor coil 32 and around conductor coil 32. Insulator 33 can define a lumen (not shown) for insertion of a stylet to stiffen the lead during implantation. The difference between the two conductors' wound diameters is typically sufficient to allow the electrical insulation of the two conductors from one another. Thus, insulator 33 electrically isolates inner conductor coil 31 from the outer conductor coil 32. An outer insulator 34 electrically isolates the conductors from the lead's environment. Alternatively, a bipolar conductor could be configured having two separate unifilar or multifilar conductors wound in parallel (not shown). The parallel wound bipolar conductor would have two alternating electrically isolated spiral wound conductors wound in parallel about the longitudinal axis and having the same wound diameter.

Figure 4:
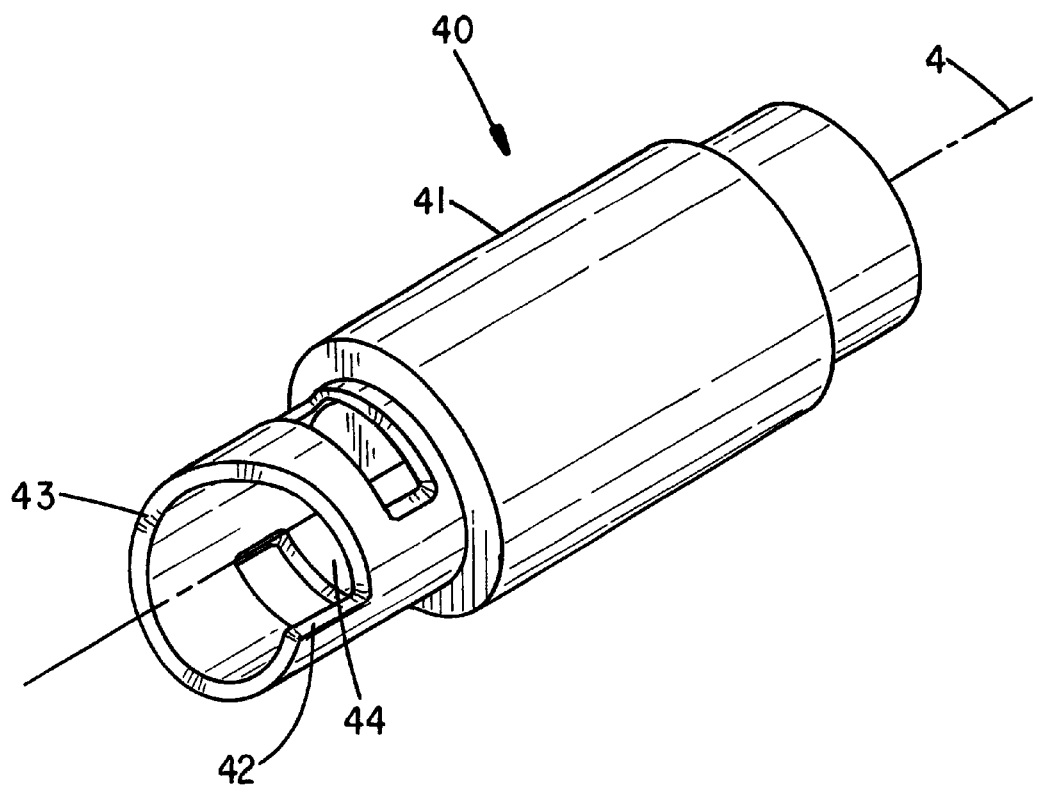
FIG. 4 is a perspective drawing illustrating an embodiment of a ring electrode.

FIG. 4 illustrates the proximal end of an electric element 40. Electric element 40 is shown as a ring electrode like electrode 16 of FIG. 1 for illustrative purposes. The proximal end of a sensing electrode, the distal end of a lead connector pin, or any other electric element would be interchangeable with the ring electrode for purposes of the present invention. Electric elements found in implantable leads are typically made from stainless steel, MP35N or other biocompatible materials. In the embodiment shown, electric element 40 includes an exposed region 41 designed to electrically contact a tissue structure. Exposed region 41 is in electrical communication with a longitudinal edge 42. Longitudinal edge 42 can be integral with or distinct from exposed region 41 depending on the nature of the particular electric element. Longitudinal edge 42 is substantially parallel to a longitudinal axis 45 of electrical element 40. Further, longitudinal edge 42 can be spaced a distance from longitudinal axis 45 substantially equivalent to winding radius of the filars. Longitudinal edge 42 is configured to allow cut ends of filars to abut to longitudinal edge 42 to facilitate an electrical connection between longitudinal edge 42 and the cut ends. Longitudinal edge 42 is also configured to allow the cut ends of the filars to be welded to longitudinal edge 42. In other embodiments, longitudinal edge 42 can be configured to allow the cut ends of the filars to be secured thereto using an electrically conductive adhesives, crimping or other methods of connecting cut ends to electric elements known to those skilled in the art. A second edge 43 can also be provided on the electric element. Second edge 43 cooperates with longitudinal edge 42 to form a notch 44. Second edge 43 may be configured with a pitch corresponding to the pitch of the wound filars. When the pitch of second edge 43 corresponds to the pitch of the wound filars, second edge 43 can contact a filar 53 (shown in FIG. 5B) over a distance 58 that the electric element and the wound filar are coextensive.

Figure 5A:
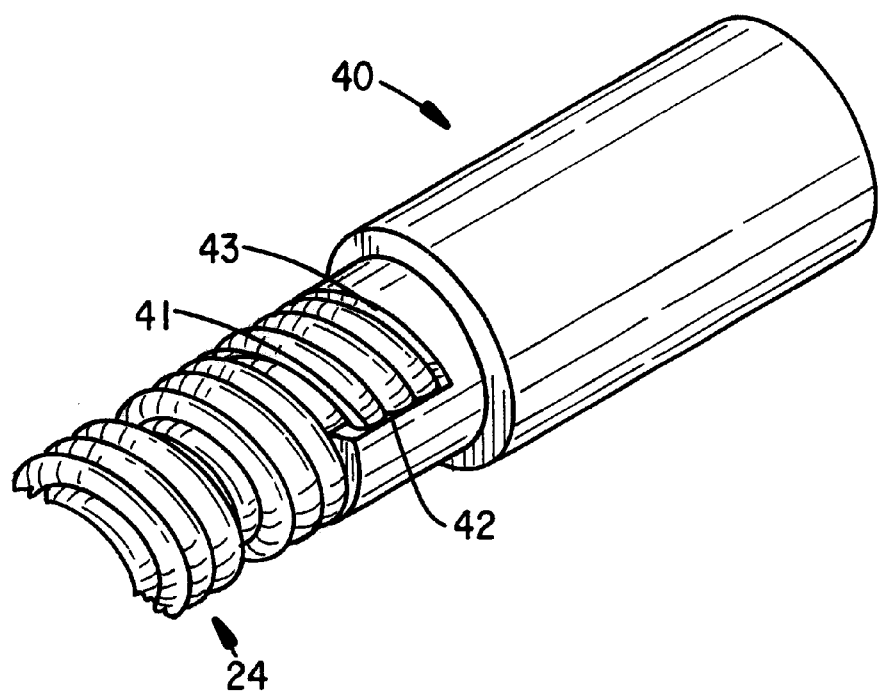
FIG. 5A is a perspective drawing illustrating an embodiment of the interconnection between the conductor and the ring electrode illustrated in FIG. 4.
Figure 5B:
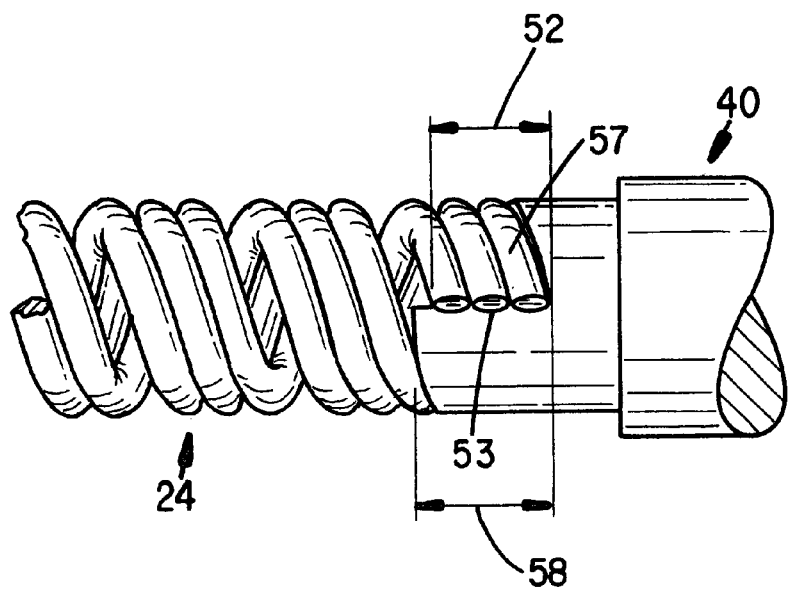
FIG. 5B is a side elevation drawing of the interconnection illustrated in FIG. 5A.

FIGS. 5A and 5B illustrate the connection between an electrical element 40 and multifilar conductor coil 24. At least one end 41 is generated by cutting the distal end of the conductor coil along the coil's longitudinal axis. The coil is typically cut by trimming, grinding, laser cutting or by other means known to those skilled in the art. When there are a plurality of ends, the ends 41 are oriented collinearly with one another. For purposes of the present invention, a plurality of collinear ends means the ends are sufficiently collinear to allow all ends to be secured to longitudinal edge 42 of electrode 40. A single collinear end means the end is cut in a configuration allowing the end to be secured longitudinal edge 42. The actual number of ends generated by cutting is typically equivalent to the number of filars in the conductor coil. That is, cutting a unifilar conductor produces one end and cutting a trifilar conductor typically produces three ends. Although, the number of ends can vary from the number of filars, such as when in bipolar conductors are wound in parallel (as described above but not shown). If the conductor has an insulator, the cutting of the conductor coil can either be preceded or followed by the removing a portion of the insulator from the cut ends. The insulator can be removed mechanically, by chemical etching, or by other methods known to those of skill in the art. Longitudinal edge 42 of electric element 40 is then secured to the at least one end 41. When ends 41 are secured to longitudinal edge 42, a mandrel (not shown) may be inserted through a lumen defined along the longitudinal axis of the conductor and the longitudinal axis of electric element 40. As discussed above, the ends can be secured by welding, electrically conductive adhesives or by other methods known to those skilled in the art. When secured by welding the ends can be secured by a single weld 53 extending over distance 52 or by a series of welds 53 extending over distance 52.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the invention's scope.

We claim:

1. A method for manufacturing an implantable lead, comprising:

providing a conductor having at least one filar and an electric element having a longitudinal edge;

cutting the at least one filar in a direction parallel to a longitudinal axis of the conductor forming at least one collinear cut end parallel with the longitudinal axis of the conductor; and securing the at least one collinear cut end to the longitudinal edge of the electric element to provide an electrical connection.

2. A method, as in claim 1, wherein the conductor includes a plurality of filars.

3. A method, as in claim 1, wherein the electric element is a ring electrode, a terminal pin, a splice ring or a terminal ring.

4. A method, as in claim 1, wherein the electric element is a lead connector pin.

5. A method, as in claim 1, wherein securing is by welding the at least one cut end to the longitudinal edge.

6. A method, as in claim 1, wherein securing is by soldering the at least one cut end to the longitudinal edge.

7. A method, as in claim 1, wherein securing is by applying an electrically conductive adhesive to the at least one cut end and the longitudinal edge.

8. A method, as in claim 1, wherein the at least one filar is spirally wound into the conductor at a substantially constant pitch.

9. A method, as in claim 8, wherein the longitudinal edge and a second edge of the electric element define a notch, the second edge configured to have a pitch corresponding to the pitch of the filars such that one filar abuts the second edge for a distance that the electric element and the conductor are coextensive.

10. A method, as in claim 1, wherein the at least one filar is embedded in an insulator.

11. A method, as in claim 10, wherein the insulator defines a lumen adapted to receive a stylet.

12. A method, as in claim 10, further comprising removing a portion of the insulator proximate to the location of the cutting prior to the cutting of the plurality of filars.

13. A method for connecting a conductor including at least one filar to an electric element, comprising:

a step for cutting the at least one spirally wound filar parallel to a longitudinal axis of the conductor to form at least one collinear cut end parallel with the longitudinal axis of the conductor; and a step for securing the at least one cut end along a longitudinal axis of the electric element.

14. A method, as in claim 13, wherein the conductor includes a plurality of filars.

15. A method, as in claim 13, wherein the electric element is a ring electrode, a terminal pin, a splice ring or a terminal ring.

16. A method, as in claim 13, wherein the electric element is a lead connector pin.

17. A method, as in claim 13, wherein the at least one filar is spirally wound into the conductor at a substantially constant pitch.

18. A method, as in claim 17, wherein the electric element includes a notch having a longitudinal edge and a second edge, the longitudinal edge forming the longitudinal axis to which the at least one cut end is secured and the second edge having a pitch corresponding to the pitch of the at least one filar, such that one of the at least one filar abuts the second edge for a distance that the electric element and the conductor are coextensive.

19. A method, as in claim 13, wherein the at least one filar is embedded in an insulator.

20. A method, as in claim 19, wherein the insulator defines a lumen adapted to receive a stylet.

21. A method, as in claim 19, further comprising a step of removing the insulator prior to the cutting of the at least one filar.

22. An implantable lead, comprising:
   a conductor having at least one filar wherein the at least one filar terminates at one end wherein the one end is collinear in a direction parallel to a long axis of the conductor; and
   an electric element having a longitudinal edge configured to contact the one end wherein the one end is secured to the longitudinal edge.

23. A lead, as in claim 22, wherein the conductor includes a plurality of filars.

24. A lead, as in claim 22, wherein the electric element is a ring electrode, a terminal pin, a splice ring or a terminal ring.

25. A lead, as in claim 22, wherein the electric element is a lead conductor pin.

26. A lead, as in claim 22, wherein the one end of the at least one filar is secured to the electric element by welding.

27. A lead, as in claim 22, wherein the one end of the at least one filar is secured to the electric element by soldering.

28. A lead, as in claim 22, wherein the one end of the at least one filar is secured to the electric element with an electrically conductive adhesive.

29. A lead, as in claim 22, wherein the at least one filar is spirally wound into the conductor at a substantially constant pitch.

30. A lead, as in claim 28, wherein the longitudinal edge and a second edge of the electric element define a notch, the second edge having a pitch corresponding to the pitch of the at least one filar such that one of the at least one filar abuts the second edge for a distance that the electric element and the conductor are coextensive.

31. An implantable lead, comprising:
   a means for conducting an electric current including at least one filar, wherein the at least one filar terminates with at least one end and the at least one end is collinear in a direction parallel to a longitudinal axis of the means for conducting an electric current;
   a means for transferring electric current defining a longitudinal edge; and
   a means for securing the at least one end along the longitudinal edge of the means for transferring an electric current.

32. A lead, as in claim 31, wherein the means for conducting an electric current includes a plurality of filars.

33. A lead, as in claim 31, wherein the at least one filar is spirally wound into the conductor at a substantially constant pitch.

34. A lead, as in claim 31, wherein the longitudinal edge and a second edge of the means for transferring an electric current define a notch, the second edge having a pitch corresponding to the pitch of the at least one filar such that one of the at least one filar abuts the second edge for a distance that the means for transferring an electric current and the means for conducting an electric current are coextensive.

35. A method for manufacturing an implantable lead, comprising:
   providing a conductor including at least one filar and an electric element including a longitudinal edge;
   cutting the at least one filar to form at least one cut end; and
   securing the at least one cut end to the longitudinal edge of the electric element.

36. A method, as in claim 35, wherein the conductor includes a plurality of filars.

37. An implantable lead, comprising:
   a conductor having at least one filar wherein the at least one filar terminates at one end; and
   an electric element having a longitudinal edge configured to contact the one end wherein the one end is secured to the longitudinal edge.

38. A lead, as in claim 37, wherein the conductor includes a plurality of filars.

* * * * *